(12) United States Patent
Chen (10) Patent No.: US 6,902,831 B2
(45) Date of Patent: Jun. 7, 2005

(54) AZULENE-BASED COMPOUNDS IN ORGANIC LIGHT EMITTING DEVICE ELEMENTS

(75) Inventor: Jian Ping Chen, Palo Alto, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 32 days.

(21) Appl. No.: 10/303,865

(22) Filed: Nov. 26, 2002

(65) Prior Publication Data

US 2004/0101711 A1 May 27, 2004

(51) Int. Cl.$^7$ .......................... H05B 33/00; C09K 11/00
(52) U.S. Cl. ..................... 428/690; 428/917; 313/504; 313/506; 252/301.16; 558/265
(58) Field of Search ................... 252/301.16; 558/265; 313/504, 506; 428/690, 917

(56) References Cited

U.S. PATENT DOCUMENTS

| | | | |
|---|---|---|---|
| 5,059,861 A | 10/1991 | Littman et al. | |
| 5,061,569 A | 10/1991 | VanSlyke et al. | 428/457 |
| 5,073,446 A | 12/1991 | Scozzafava et al. | |
| 5,100,523 A | 3/1992 | Helms et al. | |
| 5,104,749 A * | 4/1992 | Sato et al. | 428/690 |
| 5,155,566 A | 10/1992 | Nakayama et al. | 257/40 |
| 5,294,869 A | 3/1994 | Tang et al. | 313/504 |
| 6,121,322 A * | 9/2000 | Dickhaut et al. | 514/577 |
| 6,127,516 A | 10/2000 | Bard et al. | 528/396 |
| 6,280,859 B1 * | 8/2001 | Onikubo et al. | 428/690 |
| 6,355,365 B1 | 3/2002 | Hotta et al. | 428/690 |
| 6,376,655 B1 | 4/2002 | Berg et al. | 534/573 |
| 6,537,687 B1 * | 3/2003 | Nii | 428/690 |
| 6,689,491 B1 * | 2/2004 | Nii et al. | 428/690 |
| 2001/0004107 A1 | 6/2001 | Hanna et al. | |
| 2001/0033944 A1 | 10/2001 | Onikubo et al. | |
| 2003/0122479 A1 * | 7/2003 | Farrand et al. | 313/504 |

FOREIGN PATENT DOCUMENTS

| | | | |
|---|---|---|---|
| EP | 1318185 | * | 6/2003 |
| JP | 02-195681 | * | 8/1990 |

OTHER PUBLICATIONS

Shunji Ito et al., Syntheses, Properties, and Redox Behaviors of Di(1–azulenyl) ferrocenylmethyl Cations and 1,3–Bis [(1–azulenyl)ferrocenylmethylium]azulene Dication, *J. Org. Chem.*, Jul. 26, 1996, vol. 61, No. 15, pp. 5077–5082.

Shunji Ito et al., "High Stabilities of Di(1–azulenyl)(4–hydroxyphenyl)methyl Hexafluorophosphates and Polarized Properties of α,α–Di(1–azulenyl)–1,4–benzoquinone Methides", *J. Org. Chem.*, Apr. 18, 1997, vol. 62, No. 8, pp. 2423–2431.

B. R. Hsieh, Ed., "Organic Light–Emitting Materials and Devices", *Macromolecular Symposia*, Jan. 1998, vol. 125, pp. 1–48.

Rainer E. Martin et al., "Linear Monodisperse π–Conjugated Oligomers: Model Compounds for Polymers and More", *Agnew. Chem. Int. Ed.*, May 17, 1999, vol. 38, No. 10, pp. 1350–1377.

Shunji Ito et al, "Tris[6–(dimethylamino)–1–azulenyl]methyl Hexafluorophosphate. Extremely Stable Methyl Cation with the Highest $pK_R+$ Value", *J. Org. Chem.*, Aug. 6, 1999, vol. 64, No. 16, pp. 5815–5821.

Alexander J. Berresheim et al., "Polyphenylene Nanostructures", *Chem. Rev.*, Jul. 1999, vol. 99, No. 7, pp. 1747–1785.

(Continued)

Primary Examiner—Rena Dye
Assistant Examiner—Camie S Thompson
(74) Attorney, Agent, or Firm—Fitzpatrick, Cella, Harper & Scinto (57) ABSTRACT

An organic light-emitting device (OLED) in which an azulene based compound is used as an emissive layer and/or one or more charge transport layers, or as a host material, or is doped into a functional layer of an OLED to improve device efficiency.

7 Claims, 1 Drawing Sheet-

| |
|---|
| 6 |
| 5 |
| 4 |
| 3 |
| 2 |
| 1 |

OTHER PUBLICATIONS

Shunji Ito et al., "Synthesis, Properties, and Redox Behavior of Di(1-azulenyl)(2- and 3-thienyl)methyl Cations and Dications Composed of Two Di(1-azulenyl)methylium Units Connected with 2,5-Thiophenediyl and 2,5-Thienothiophenediyl Spacers", *J. Org. Chem.*, 2001, vol. 66, No. 7, pp. 2470–2479.

Shunji Ito et al, "Synthesis and Redox Behaviour of Azulene–Substituted Benzene Derivatives and ($\eta^5$–Cyclopentadienyl)[tetra– and di(6–azulenyl)cyclobutadiene]cobalt Complexes,", *J. Org. Chem.*, 2001, vol. 66, No. 21, pp. 7090–7101.

* cited by examiner

| 6 |
|---|
| 5 |
| 4 |
| 3 |
| 2 |
| 1 |

Figure 1

AZULENE-BASED COMPOUNDS IN ORGANIC LIGHT EMITTING DEVICE ELEMENTS

BACKGROUND OF THE INVENTION

1. Field of the Invention

The present invention relates to elements for organic light emitting devices (OLEDs) in which an azulene-based compound is used in the emissive layer and/or one or more of the charge transport layers, or as a host material for one or more of such layers.

2. Description of the Related Art

Organic light emitting devices (OLEDs) typically comprise a layer of emissive material between an anode and a cathode. When a bias is applied across the electrodes, positive charges (holes) and negative charges (electrons) are respectively injected from the anode and cathode into the emissive layer. The holes and the electrons form excitons in the emissive layer to emit light.

Electrodes are chosen to facilitate charge injection. A transparent indium-tin-oxide (ITO) anode has a relatively high work function and is therefore suitable for use as a hole injection electrode, while low work function metals such as Al, Mg and Ca are suitable for injection of electrons.

To improve the power efficiency of an OLED, it is frequently desirable to enhance charge injection at the electrode interface. Hole transport layers and electron transport layers may be added adjacent the respective electrodes to facilitate charge transfer. Depending upon whether hole transport or electron transport is favored, the light emissive layer may be located closer to the anode or the cathode. In some instances, the emissive layer is located within the hole transport or electron transport layer.

Improved performance can be obtained if blocking layers are provided to block against the injection of either holes or electrons from the adjoining layer and their subsequent escape from the device. Likewise, a modifying layer may be used to improve the contact with one or both of the electrodes, or to improve the interface between two other layers.

Some of these layers can be combined. For example, a double-layered structure is fabricated from a combined hole-injecting and transporting layer together with a combined electron-transporting and light-emitting layer. Likewise, a triple-layered structure is composed of a hole-injecting and transporting layer, a light-emitting layer, and an electron-injecting and transporting layer.

Hole transport layers may include triarylamine-based materials, although many other hole transport materials are known. Likewise, an aluminum quinolinolate complex known as AlQ3 is a well known electron-transport material which has been used in OLEDs, although other electron transport materials are known.

Emissive materials having widely varied structures are known in the art and are generally selected based on color, brightness, efficiency and lifetime. These emissive materials may themselves also have electron transport or hole transport characteristics.

In addition, it is possible to form these layers from a host material doped with another material designed to achieve the desired effect of the layer (for example, to achieve a hole transport effect, an electron transport effect, or an emissive effect).

There continues to be a need for suitable materials having bright, high purity luminescent emission, and for materials which contribute to greater luminescence per injected charge.

SUMMARY OF THE INVENTION

In one aspect, the invention is an organic light emitting device comprising an anode, a cathode and at least one functional layer interposed between the anode and the cathode and comprising an azulene-based compound with the following structure:

(I)

In the above formula, each of $R_1$ through $R_7$ is independently hydrogen, hydroxy, amino, mercapto, carboxyl, nitro, cyano, azido, or halo, or an alkyl, alkenyl, alkynyl, alkoxy, alkenyloxy, alkynyloxy, aromatic, or heteroaromatic group, which group(s) may be substituted or unsubstituted. Ar is an n-valent radical comprising at least one aromatic or heteroaromatic group, which group(s) may also be substituted or unsubstituted. The number ("n") of azulene-based groups attached to the core Ar is at least one and has an upper limit defined by the valency of Ar. For example, if Ar is benzene, n is 1 to 6. In embodiments, the layer(s) comprising the azulene-based compound is an emissive layer. In other embodiments, the azulene-based functional layer is a hole transport or electron transport layer, in which case the OLED will require an emissive layer in addition to the azulene-based functional layer. Many azulene based compounds also make suitable hosts, which may be combined with functional (emissive or charge transport) guest materials in a guest-host system in an OLED.

In another aspect, the invention is a method for improving the efficiency of an OLED by doping a functional layer (i.e. an emissive layer, an electron transport layer, a hole transport layer, or a layer combining these functionalities) with azulene or a compound having a substituted or unsubstituted azulene moiety, in an amount effective to improve the efficiency of the device relative to an undoped device.

This brief summary has been provided so that the nature of the invention may be understood quickly. A more complete understanding of the invention can be obtained by reference to the following detailed description of the preferred embodiments thereof in connection with the attached figure.

DETAILED DESCRIPTION OF THE PREFERRED EMBODIMENTS

Azulene has the following structure:

The fused seven ring/five ring structure results in polariztion which yields remarkably stabilized anions and cations. Consequently, the azulene-based materials described herein are useful as host materials, electron-transport materials, hole transport materials, and emissive materials where the effectiveness of the materials relies on a redox mechanism.

In embodiments according to the invention, azulene or a compound having a substituted or unsubstituted azulene moiety is doped into an emissive or charge transport layer of an OLED to improve device efficiency. Preferably, the compounds are co-evaporated and co-deposited using thermal evaporation vacuum techniques in an amount between about 0.5 to about 2 percent by weight with respect to the functional layer in which the azulene based compound is doped. For example, an azulene-based compound can be codeposited with a metal complex, such as AlQ3 using thermal evaporation techniques. Any azulene-based compound may be used in this manner to improve device efficiency in an OLED. Particular examples are provided in Formulas I through XVII below.

The numbering system for azulene shown above is commonly used to describe the eight substitutable carbon atoms in the azulene ring structure. However, in the compounds of the present invention, one or more azulene moieties is bonded to a core Ar, and the substitutable carbon atoms on the azulene portion of the structure are numbered $R_1$ through $R_7$ in clockwise fashion, starting from the carbon atom adjacent to the carbon atom bonded to the core. In Formulas I through XVII below, the azulene is functionalized at the 6 position.

A method of forming a benzene ring substituted with azulene moieties functionalized at the 6 position is disclosed in S. Ito, et al. "Synthesis and Redox of Azulene-Substituted Benzene Derivatives and ($\eta^5$-Cyclopentadienyl)[tetra- and di(6-azulenyl)cyclobutadiene]cobalt complexes," *J. Org. Chem.* 201, 66, 7090–7101(2001). In that method, 6-azulenylacetylene is formed starting from 6-bromoazulene, and 6-azulenylacetylene undergoes a Diels-Alder reaction with tetraphenylcyclopentadienone to form a substituted benzene ring.

The positions $R_1$ through $R_7$ (and $R_{1'}$ through $R_{7'}$, etc., as the case may be depending on the number of azulene groups attached to the core (Ar)) may be occupied by hydrogen, or these positions may be substituted. Suitable substituents for $R_1$ through $R_7$ may be selected from those disclosed in U.S. Pat. No. 6,121,322, herein incorporated by reference. Thus, any of $R_1$ through $R_7$ independently may be hydroxy, amino, mercapto, carboxyl (including carboxylate), nitro, cyano, azido, or halo. Further, any of $R_1$ through $R_7$ may be substitutable moieties such as alkyl, alkenyl, alkynyl, alkoxy, alkenyloxy, alkynyloxy, aromatic, or heteroaromatic group, and any of said groups may be independently substituted or unsubstituted. Thus, for example, "alkyl" covers a branched, linear or ring saturated hydrocarbon chain which may have one or more of the hydrogen atoms on the chain substituted with an atom or group other than hydrogen, including hydroxy, halo, amino, nitro, cyano, azido, mercapto, sulphinyl, sulphonyl, carboxyl and carbonyl groups.

For example, and not by way of limitation, the substituent groups $R_1$–$R_7$ may be relatively electron-rich species such as alkyl or alkoxy, preferably lower (C1–C8) alkyl or alkoxy, including methyl, methoxy, ethyl, ethoxy, tert-butyl or tert-butoxy. These and other electron rich species may serve to stabilize the cationic form of the azulene based compound. The alkyl or alkoxy groups may themselves be substituted.

As another example, and not by way of limitation, the substituent groups $R_1$–$R_7$ may also be electron withdrawing species, such as a carboxy group, preferably a carboxylate ester wherein the ester group is a lower (C1–C8) alkyl, including without limitation methylcarboxylate (—COOMe) and ethylcarboxylate (—COOEt). In embodiments, $R_3$ and $R_5$ are ethylcarboxylate, thus providing electron withdrawing species on the more negatively charged five membered ring. Such species may serve to stabilize the anionic form of the azulene-based compound.

Other suitable substituent groups include alkenyl, alkynyl, alkenyloxy, alkynyloxy, aromatic and heteroaromatic groups, which groups may be substituted or unsubstituted, and which may be selected based on their electronic or steric contribution to the compound. Thus, for example, alkenyl covers a hydrocarbon chain with at least one double bond, which may have an atom or group other than hydrogen substituted on the chain, including without limitation, hydroxy, halo, amino, nitro, cyano, azido, mercapto, sulphinyl, sulphonyl, carboxyl and carbonyl groups.

In summary, the substituent groups that may be attached the azulene moieties or to free positions on the core Ar are limited only by the ability to synthesize the desired compound.

Thus a single azulene-based group may be functionalized at the 6 position and bonded to a single ring aromatic core (Ar) as in Formula II.

(II)

Alternatively, two or more azulene-based groups may be bonded to a single-ring core as in Formulas III to V.

(III)

(IV)

(V)

One of ordinary skill in the art will recognize that any of the unnumbered substitutable carbon atoms on the azulene moieties in Formula (V) above may be independently substituted with $R_1$ through $R_7$, according to general Formula (I). As a practical matter, it is often the case that all of the substituent azulene moieties are identical. The compounds of Formulas III to V absorb at 600–1200 nm and would likely make suitable hosts in guest-host systems, permitting efficient, stabilized energy transfer to guest compounds.

Alternatively, one or more azulene moieties may be bonded to a core having multiple fused aromatic rings. The resulting compounds are likely candidates to form emissive materials, due to the high degree of conjugation in the core. For example, a core Ar may be formed of naphthalene, as in Formula VI.

(VI)

As with the smaller aromatic or heteroaromatic cores, a multi-ring core Ar may be bonded to multiple azulene or azulene-based groups. Examples are shown in Formulas VII, VIII and IX.

(VII)

(VIII)

(IX)

Known emissive chemical structures, such as fluorene, may be adapted with azulene-based substituents to form stabilized emissive materials for use in OLEDs. Examples include Formulas X and XI.

(X)

(XI)

wherein R' and R" can be substituted in the same manner as set forth above for $R_1$ through $R_7$, based on information relating to emissive fluorene derivatives available in the prior art.

In embodiments, the core (Ar) may comprise a hole-transport moiety, such as triphenylamine to provide an azulene based compound having hole transport capability, as in Formula XII.

(XII)

Likewise, the aromatic core (Ar) may consist of heteroaromatic multi-ring structures such as triphenyl triazine shown in Formula XIII. The azine moiety has electron transport capability. Therefore, the resulting azulene-based compounds incorporating azine are expected to have hole transport capability.

(XIII)

As in the previous examples, any of the carbon atoms on the azulene rings in Formulas XII or XIII may be independently substituted in the same manner as set forth above for $R_1$ through $R_7$.

In still further embodiments, the core (Ar) may comprise a single atom of carbon or silicon to which aromatic groups are bonded as in Formula XIV and Formula XV.

(XIV)

(XV)

The materials of formulas XIV and XV are expected to provide stability and energy transfer to a guest material. Therefore, these are good candidates for host materials.

It will be readily understood by those having ordinary skill in the art that the substitutable carbon atoms on the core (Ar) in any of the foregoing Formulas, which are not bonded to azulene-based groups and which are not shown as bearing optional substituents, could nevertheless be substituted in the same manner as set forth above for $R_1$ through $R_7$.

An example where the core (Ar) is heteroaromatic is shown in Formula XVI, wherein Ar is thiophene.

(XVI)

The core (Ar) moiety could also be based on other heteroaromatic species, including without limitation, pyrrole, pyrazole, triazole, imidazole, dithiole, oxazole, oxathiazole, thiazole, pyran, pyridine, pyrimidine, pyrazine, oxazine, and fused ring species incorporating any of these.

An example where the core (Ar) comprises ethynyl linkages on an aromatic core is shown in Formula XVI.

(XVII)

Devices according to the invention find use in display applications such as television screens, computer screens and image bar components for digital copiers and printers, although the invention is not limited to these uses.

Figure 1:
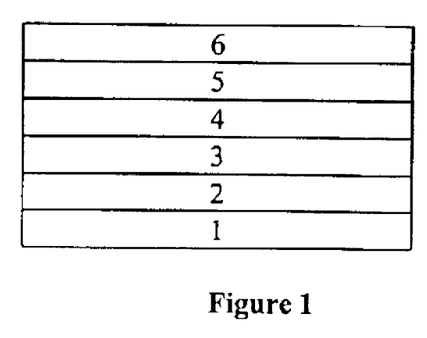
FIG. 1 is a schematic cross-sectional view of an EL device according to the invention.

FIG. 1 schematically depicts an OLED, including substrate 1, anode 2 adjacent the substrate, optional hole injection layer 3 adjacent the anode, emissive layer 4, optional electron transport layer 5 adjacent the emissive layer, and cathode 6. Each of these layers may itself comprise multiple layers of material having similar composition or function. Functional layers may also be combined. For example, an emissive layer may be adapted to exhibit electron transport properties. Optional modifying layers can be interposed between any two functional layers 1 through 6 without departing from the scope of the invention. For example, a buffer layer can be provided between the electrodes and the adjacent charge transfer layers to suppress leakage currents.

OLEDs according to the invention may have a driving voltage between 0.1 V and 100 V, preferably between 1 V and 15 V, producing a current density at the anode/hole injection layer interface in a range of about 0.01 mA/cm$^2$ to about 1000 mA/cm$^2$.

Suitable materials for substrate 1 include glass, quartz and the like, and polymers (including, without limitation, polyesters, polycarbonates, polyacrylates, polymethacrylates, and polysulfones). The thickness of the substrate is not critical and can range, for example, from about 25 to over 1,000 microns, depending on the structural demands of the device. The substrate is preferably transparent.

The anode adjacent the substrate can be comprised of a metal, an alloy, an electroconducting compound, or mixtures thereof, with a work function preferably equal to or greater than about 4.0 electron volts. Specific examples of anodes include hole injecting electrodes such as indium tin oxide (ITO), tin oxide, zinc oxide, gold, platinum, electrically conductive carbon, and conjugated polymers such as polyaniline, polypyrrole, and the like. At least one of the anode and the cathode must be transparent to produce a functioning OLED. ITO is preferred, as it has good transparency to visible light. The thickness of the anode can range anywhere from about 10 nanometers to 1 micron or more The anode may be deposited by sputtering, or other method of thin film deposition known in the art, preferably thermal evaporative deposition under high vacuum.

A relatively thin modifying layer (not shown) such as copper phthalocyanine (CuPc) may be used to improve the transport of holes from the anode to the region where charges combine to form excitons, as known in the art.

A hole transporting layer 3 having a thickness in the range of 10 Angstroms to 1000 Angstroms or more may be deposited directly on the anode or on a modifying layer. Well known hole transport materials include N,N'-diphenyl-N,N'-bis(3-methylphenyl) (1,1'-biphenyl) 4,4'-diamine (TPD), N,N,N',N'-tetrakis (4-methylphenyl) (1,1'-biphenyl)-4,4'-diamine (TTB), and N,N'-bis-(1-naphthyl)-N,N'-diphenyl-1,1'-biphenyl-4,4'-diamine (NPB), which are widely used in current OLED research. However, the invention is not limited to the use of these materials.

Suitable luminescent materials for use in an OLED according to the invention include the materials heretofore described in the art as being useful for this purpose, including without limitation the materials described in B. R. Hsieh, Ed., "Organic Light-Emitting Materials and Devices," *Macromolecular Symposia*, Vol. 125, pp. 1–48 (January, 1998) and U.S. Pat. No. 5,294,869, which is herein incorporated by reference. However, the invention is not limited to the use of these materials. Luminescent layer 4 may have a thickness in the range of 10 Angstroms to 1000 Angstroms or more.

An electron transport layer 5 having a thickness in the range of 10 Angstroms to 1000 Angstroms or more may be selected from the many suitable materials known in the art. The best known electron transport materials are metal chelates such as AlQ$_3$, and BeBq$_2$, 1,3,4-oxiazole derivatives (OXDs) such as PBD, and 1,2,4-triazoles (TAZs). However, the invention is not limited to the use of these materials.

For thin-film EL devices, evaporated metal films are generally used for the electron injecting contact 6, mainly because they can be applied in a controlled atmosphere onto a large area. Evaporated Mg alloyed with a small amount of silver is an excellent choice and has a low enough work function. Al, Ca, and Li:Al alloy may also be used.

Any electron injecting, electron transport, and electron transport/luminescent, hole transport/luminescent, charge blocking, or buffer layer known to be useful in OLED manufacture may be employed in an OLED according to the invention.

Most of the azulene compounds falling within the foregoing description absorb at wavelengths in the 550 to 1200 nm range. Where fluorescent emission is observed, emissions tend to be at wavelengths in the 600–1200 nm range.

The compounds falling within the foregoing description are "small molecules" as compared to polymers, and therefore they can be thermally evaporated under high vacuum (10$^{-5}$ to 10$^{-7}$ torr) and deposited as thin films. The following Examples of OLED manufacture are illustrative:

EXAMPLE 1

An indium tin oxide (ITO) anode material is patterned on a glass substrate and a layer of TPD having hole transport capability is vacuum deposited on the anode such that the combined anode and hole transport layers have a thickness in the range of 10 to 50 nm. An azulene-based compound is selected and likewise thermally evaporated to form a layer having a thickness in the range of 20 to 60 nm. An AlQ3 electron transport layer is vacuum deposited to a thickness of 10–30 nm, followed by a very thin (0.5–1.5 nm) LiF contact modification layer and finally an Al cathode having a thickness in the range of 100–300 nm. Upon application of a forward bias, a red luminescent emission is observed.

EXAMPLE 2

The procedure for making an OLED described in Example 1 is repeated, except that the emissive layer comprises an AlQ3 host compound doped with about 0.5 to about 2 percent by weight of an azulene-based compound to improve device efficiency.

The foregoing examples are for illustration purposes and are not to be considered limiting of the invention, which is defined by the following claims.

What is claimed is:

1. An organic light emitting device comprising an anode, a cathode and at least one emissive layer interposed between the anode and the cathode, said emissive layer comprising an azulene-based compound selected from the group consisting of:

(VI)

(VII)

(VIII)

and (IX)

wherein each $R_1$ through $R_7$ and $R_{1'}$ through $R_{7'}$ is independently hydrogen or hydroxy, or an alkyl, alkenyl, alkynyl, alkoxy, aromatic, or heteroaromatic group, and any of said groups may be independently substituted or unsubstituted.

2. An organic light emitting device comprising an anode, a cathode and at least one emissive layer interposed between the anode and the cathode, said emissive layer comprising an azulene-based compound selected from the group consisting of:

(XII)

, and (XIII)

wherein each of $R_1$ through $R_7$ and $R_{1'}$ through $R_{7'}$ is independently hydrogen, hydroxy, amino, mercapto, carboxyl, nitro, cyano, azido, or halo, or an alkyl, alkenyl, alkynyl, alkoxy, alkenyloxy, alkynyloxy, aromatic, or heteroaromatic group, and any of said groups may be independently substituted or unsubstituted; and wherein each of R' and R" is independently hydrogen or hydroxy, or an alkyl, alkoxy, or aromatic group, which group may be substituted or unsubstituted.

3. An organic light emitting device comprising an anode, a cathode and at least one functional layer interposed between the anode and the cathode, said functional layer being a hole transport layer comprising an azulene-based compound having the following structure:

(X)

wherein each of $R_1$ through $R_8$, $R_{1'}$ through $R_{7'}$ and $R_{1''}$ through $R_{7''}$ is independently hydrogen or hydroxy, or an alkyl, alkoxy, aromatic, or heteroaromatic group, and any of said groups may be independently substituted or unsubstituted.

4. An organic light emitting device comprising an anode, a cathode and at least one functional layer interposed between the anode and the cathode, said functional layer being an electron transport layer comprising an azulene-based compound having the following structure:

(XI)

wherein each of $R_1$ through $R_7$, $R_{1'}$ through $R_{7'}$ and $R_{1''}$ through $R_{7''}$ is independently hydrogen or hydroxy, or an alkyl, alkenyl, alkynyl, alkoxy, aromatic, or heteroaromatic group, and any of said groups may be independently substituted or unsubstituted.

5. An organic light emitting device comprising an anode, a cathode and at least one functional layer interposed between the anode and the cathode, said functional layer comprising an azulene-based compound having the following structure:

wherein each of $R_1$ through $R_7$ is independently hydrogen, hydroxy, amino, mercapto, carboxyl, nitro, cyano, azido, or halo, or an alkyl, alkenyl, alkynyl, alkoxy, alkenyloxy, alkynyloxy, aromatic, or heteroaromatic group, and any of said groups may be independently substituted or unsubstituted;
wherein Ar is a single benzene ring, and
n is 1 to 6.

6. An organic light emitting device comprising an anode, a cathode and at least one functional layer interposed between the anode and the cathode, said functional layer comprising an azulene-based compound having the following structure:

wherein each of $R_1$ through $R_7$ is independently hydrogen, hydroxy, amino, mercapto, carboxyl, nitro, cyano, azido, or halo, or an alkyl, alkenyl, alkynyl, alkoxy, alkenyloxy, alkynyloxy, aromatic, or heteroaromatic group, and any of said groups may be independently substituted or unsubstituted; and
wherein Ar is a single thiophene ring, and
n is 1 to 4.

7. An organic light emitting device comprising an anode, a cathode and at least one functional layer interposed between the anode and the cathode, said functional layer comprising an azulene-based compound having the following structure:

wherein each of $R_1$ through $R_7$ is independently hydrogen, hydroxy, amino, mercapto, carboxyl, nitro, cyano, azido, or halo, or an alkyl, alkenyl, alkynyl, alkoxy, alkenyloxy, alkynyloxy, aromatic, or heteroaromatic group, and any of said groups may be independently substituted or unsubstituted; and
wherein Ar is tetraphenylmethane or tetraphenylsilane, and
n is 1 to 4.

* * * * *

UNITED STATES PATENT AND TRADEMARK OFFICE
CERTIFICATE OF CORRECTION

PATENT NO. : 6,902,831 B2
DATED : June 7, 2005
INVENTOR(S) : Jian Ping Chen

It is certified that error appears in the above-identified patent and that said Letters Patent is hereby corrected as shown below:

Column 3,
Line 54, "$R_1$, through $R_7$," should read -- $R_{1'}$ through $R_{7'}$, --.

Column 4,
Line 36, "attached" should read -- attached to --.

Column 10,
Line 3, "more" should read -- more. --.

Column 12,
Line 60, "$R_8$" should read -- $R_7$ --.

Signed and Sealed this

Third Day of January, 2006

JON W. DUDAS
*Director of the United States Patent and Trademark Office*